US012727762B2

(12) United States Patent
Anders et al.

(10) Patent No.: US 12,727,762 B2
(45) Date of Patent: Sep. 8, 2026

(54) ILLUMINATION SYSTEM AND MEDICAL IMAGING SYSTEM FOR FLUORESCENCE IMAGING IN OPEN SURGERY

(71) Applicant: OLYMPUS Winter & Ibe GmbH, Hamburg (DE)

(72) Inventors: Konrad Anders, Hamburg (DE); Matthias Dissel, Hamburg (DE); Carsten Holthaus, Barsbuettel (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 358 days.

(21) Appl. No.: 18/388,335

(22) Filed: Nov. 9, 2023

(65) Prior Publication Data

US 2024/0268674 A1 Aug. 15, 2024

Related U.S. Application Data

(60) Provisional application No. 63/444,622, filed on Feb. 10, 2023.

(51) Int. Cl.

| | |
|---|---|
| ***A61B 5/00*** | (2006.01) |
| ***A61B 1/06*** | (2006.01) |
| ***A61B 1/07*** | (2006.01) |
| ***A61B 90/00*** | (2016.01) |
| ***A61B 90/30*** | (2016.01) |

(52) U.S. Cl.

CPC .............. *A61B 5/0071* (2013.01); *A61B 1/06* (2013.01); *A61B 1/07* (2013.01); *A61B 90/30* (2016.02); *A61B 90/36* (2016.02); *A61B 2090/306* (2016.02); *A61B 2090/3614* (2016.02)

(58) Field of Classification Search

CPC . A61B 5/0071; A61B 90/30; A61B 2090/306; A61B 1/06; A61B 1/07; A61B 90/36; A61B 2090/3614

USPC .................................................. 362/572, 574

See application file for complete search history.

(56) References Cited

U.S. PATENT DOCUMENTS

| | | | | |
|---|---|---|---|---|
| 2010/0080016 A1* | 4/2010 | Fukui | G02B 23/2469 | 362/574 |
| 2011/0141763 A1* | 6/2011 | Kamee | G02B 6/0008 | 362/583 |
| 2015/0241634 A1 | 8/2015 | Coutard et al. | | |
| 2019/0175005 A1* | 6/2019 | Tanaka | A61B 1/00165 | |
| 2019/0246888 A1* | 8/2019 | Tamura | H01S 5/4093 | |

* cited by examiner

*Primary Examiner* — Laura K Tso

(74) *Attorney, Agent, or Firm* — Scully, Scott, Murphy & Presser, P.C.

(57) ABSTRACT

An illumination system for fluorescence imaging in open surgery including an illumination light source for generating illumination light including white light and fluorescence excitation light, and illumination optics for illuminating an operating area with the illumination light. The illumination optics including a light guide configured for guiding illumination light from the illumination light source into a light entry end of the illumination optics along a light path to a light exit end of the illumination optics. The light guide includes a light guiding taper arranged in the light path comprising a light entry surface oriented towards or at the light entry end and a light emitting surface oriented towards or at the light exit end, wherein an area of the light emitting surface is larger than an area of the light entry surface.

21 Claims, 4 Drawing Sheets

5
50
3
33
30
2
35
1
20
34
22
21
70

111
110
114
104
102
106
112
116
100

3
45
36
46
30
45
47
17
11
35
31
10
15
13
14
12
16
22
41
40
42
21
40

5
61
45
10
40
6
62
8

65
40
64

65
40
10
64

ILLUMINATION SYSTEM AND MEDICAL IMAGING SYSTEM FOR FLUORESCENCE IMAGING IN OPEN SURGERY

CROSS-REFERENCE TO RELATED APPLICATION

The present application is based upon and claims the benefit of priority from U.S. Provisional Application No. 63/444,622 filed on Feb. 10, 2023, the entire contents of which is incorporated herein by reference.

BACKGROUND

Field

The present disclosure relates to an illumination system for fluorescence imaging in open surgery, as well as to an imaging system for fluorescence imaging in open surgery comprising the illumination system.

Prior Art

In open surgery, video capturing units are often placed in the operating room to record the operating area. Such video capturing units usually comprise a camera head augmented by an optical imaging unit and an illumination unit.

A camera head usually comprises one or more optical sensors as well as a cone adapter connecting and securing the ocular cones of optical imaging units to the camera head. Such optical imaging units may be devices for endoscopic procedures, such as rigid telescope type endoscopes having an optical assembly at their distal tip for forming an image of the specified field of view, and one or more relay lens units for relaying the image to the endoscope's ocular for view with the unaided eye, or alternatively, the camera head. For this purpose, the camera head comprises imaging optics that focus on the location of the virtual image projected by the ocular lens of the attached telescopes at their own focal distance. This focal distance is standardized between different types of telescopes, since they have to be usable with the unaided eye.

For the purpose of capturing the operating area, the optical imaging units are often designed to image the operating area with a predefined field of view at a predefined working distance. A typical example is the so-called exoscope, which resembles a short endoscope with an objective lens, a set of relay lens units and an eyepiece. The optical properties of the objective lens are quite different from those of objective lenses of endoscopes because of their very different focal lengths, since, unlike an endoscope, an exoscope is designed to operate outside a human body instead of inside the human body.

Since the camera head has its own imaging optics, an attachment lens system, also called a head lens, may be attached to the camera head's cone adapter that provides the combined optical system of the attachment lens system and the camera head's optical imaging system with the focal length and other optical properties necessary for viewing and recording the operating area.

In order to illuminate the operating area, the medical imaging systems usually comprise an illumination light generating unit comprising one or more light sources generating the illumination light. The illumination light is transported from the illumination light generating unit to the distal end of an optical imaging unit through a fiber bundle, where it exits the fiber bundle. Endoscopes and exoscopes usually do not comprise any light shaping units at the tip, so that the irradiance distribution at the field of operation is mainly defined by the irradiance distribution with which the light enters the fiber bundle from the light source.

Modern medical imaging systems implement the above-described versatility of endoscopic or open surgery imaging with various telescopes and exoscopes for different applications that can be attached to the system's camera head, which is controlled by a central control unit (CCU). The telescopes and exoscopes may have an illumination light connector to be connected to an illumination light generating unit of the medical imaging system via light fibers. Such systems may furthermore implement fluorescence imaging for fluorescence imaging guided surgery.

Fluorescence imaging is a form of molecular imaging, which generally encompasses imaging methods for visualizing and/or tracking of molecules having specific properties that are used for molecular imaging. Such molecules can be substances that are endogenous to the body, or dyes or contrast agents that are injected into the patient. MRI and CT, for example, therefore, also fall under the term "molecular imaging". Fluorescence imaging as a variant of molecular imaging uses the property of certain molecules (fluorophores), which emit light of certain wavelengths when excited/absorbed by light of certain wavelengths.

For the purpose of fluorescence imaging, the system's camera head includes sensors that are sensitive in the visible spectrum and in the near infrared spectrum, while the system's illumination light generating unit has a light source for white light to illuminate the operating area with white light as well as at least one excitation light source designed to illuminate the operating area with light that includes an excitation wavelength capable of exciting a fluorescent substance or dye that has been injected into the operating area, to return fluorescence emission. The excitation light source may comprise a laser or a light emitting diode, the wavelength depending on the dye used. For indocyanine green (ICG), e.g., which emits fluorescence light between 750 nm and 950 nm, an excitation wavelength may be between 600 nm and 800 nm. After being excited, the dyes shed the excitation energy by emitting light at slightly longer wavelengths than the excitation light. Other wavelengths may be used as excitation wavelengths depending on the type of dye used. This can include wavelengths that are further inside the visible spectrum.

Since the fluorescence light is typically much weaker than the white light reflected from the tissue that is being operated on, it is necessary to provide means and methods to enhance, separate or isolate the fluorescence light signal from the white light signal, as well as to prevent the fluorescence light signal from being drowned out by the excitation light.

In some medical imaging systems, for example, this may be done by time multiplexing, i.e., the alternating of white light and excitation light illumination. While this method provides a good separation, it may be found irritating by sensitive personnel due to a high speed flicker of the illumination light or a slow repetition rate of the images produced therewith.

SUMMARY

An object is to provide improved means for illumination in fluorescence imaging guided open surgery.

Such object can be solved by an illumination system for fluorescence imaging in open surgery, comprising an illumination light source configured to generate illumination light including white light and fluorescence excitation light, and illumination optics for illuminating an operating area with the illumination light generated by the illumination light source, the illumination optics comprising a light guide configured for guiding illumination light from the illumination light source coupled into a light entry end of the illumination optics along a light path of the illumination optics to a light exit end of the illumination optics, wherein the light guide can comprise a light guiding taper arranged in the light path, the light guiding taper comprising a light entry surface oriented towards or located at the light entry end of the illumination optics and a light emitting surface oriented towards or located at the light exit end of the illumination optics, wherein an area of the light emitting surface is larger than an area of the light entry surface.

Such an illumination system can be used within a medical imaging system comprising a medical imaging device such as an exoscope or a camera head augmented by an open surgery adapter having attachment optics that provide the imaging optics of the camera head with a focal length and focal depth adapted to the needs of viewing an open surgery operating area, or other suitable medical imaging devices such as a dedicated camera.

The illumination system can be based on an illumination light source that is commonly present in medical imaging systems capable of performing molecular or fluorescence imaging in addition to white light imaging. Such light sources are typically connected to a medical imaging device, such as a video endoscope, an exoscope or a camera head that can be connected to various endoscopes, exoscopes or other optical imaging devices, by means of a light guide cable, which frequently comprises a bundle of light guide fibers.

The illumination optics of endoscopes can emit illumination light under a broad angular distribution. The broad angular distribution is partly generated by the illumination light source itself. While the typical broad angle illumination is well-suited for endoscopic procedures inside the human body, where the surgeon relies on a sufficient illumination of the surroundings of the immediate field of view in order to retain his or her orientation, which means that a broad angle illumination commensurate to the large field of view present at the short distances between tissue and endoscope optics is provided, and this illumination intensity is high, it is mismatched in the case of open surgery, where the additional illumination cannot be observed outside of the field of view of the medical imaging device and therefore is lost for all practical purposes.

This results in a low light intensity where the light is actually required. This problem is amplified in fluorescence imaging guided surgery. In this context, low light intensities are especially problematic, because a high intensity of excitation light is required to create sufficient fluorescence light.

Alternatively a lens unit for narrowing the illumination light cone at the front of the medical imaging device can be employed. However, such a lens unit can be difficult to manufacture, has high manufacturing costs and creates problems when disinfecting the medical imaging device in an autoclave.

By arranging a light guiding taper in the light path, the solid angle of the light exiting the light emitting surface is decreased compared to the solid angle of the light entering the light guiding taper through the light entry surface. This effect can be achieved by the conservation of Etendue. According to this principle, a mathematical product of an illumination area and a solid angle of illuminance remains constant in an illumination chain, subject to minor losses due to the limits of total internal reflection inside the light guide, apertures and other causes of loss of light. Because of the conservation of Etendue, the larger area of the light emitting surface results in a smaller solid angle of illuminance from this surface. Thus, after exiting the light emitting surface, the light emitted by the exoscope tip will have a more narrow irradiance distribution. This increases the light intensity in the field of view of the medical imaging device.

When light travels along the light path from the light entry end to the light exit end, the light enters the light guiding taper through the light entry surface and exits the light guiding taper through the light emitting surface. The direction from the light entry end to the light exit end is called a direction of light propagation. The light exit end may be arranged in the tip or distal end of the medical imaging device. The light entry end may be arranged anywhere along the illumination light path, e.g., at a light guide cable connector of the medical imaging device, at a light source connector of a light guide cable connected to the exoscope body or even at the light source itself.

The light guiding taper can be a solid of revolution, wherein an axis of revolution of the light guiding taper can be perpendicular to the light entry surface and/or the light emitting surface. The light guiding taper can comprise a lateral surface connecting the light entry surface and the light emitting surface. The length of the light guiding taper can be between 5 and 125 mm, the diameter of the end faces of the light guiding taper can be between 1 and 20 mm.

The illumination optics can be an illumination unit or a part of an illumination unit of the medical imaging device. The medical imaging device can comprise an optical imaging unit for observing the operating area. In an embodiment, the optical imaging unit can comprise an objective lens, a set of relay lenses and an eyepiece. Such optical imaging units are known in the art. In another embodiment, the optical imaging unit can comprise a camera head having an imaging optics adapted to receive a virtual image from a telescope type endoscope or exoscope or an optics adapter comprising an attachment lens for altering the optical properties of the camera head optics, like the field of view and focal length.

The light entry surface and/or the light emitting surface can be circular. A circular surface of the light guiding taper can be provided, because light can be transmitted from a fiber bundle to the taper and/or from the taper to the fiber bundle without a significant loss of light intensity. According to the present disclosure, the diameter of the light emitting surface can be larger than a diameter of the light entry surface.

The light entry surface and the light emitting surface can be parallel to each other. Parallel surfaces can provide a simple and effective way of guiding the light through the light guiding taper. The light entry surface and/or the light emitting surface can be planar. Planar surfaces can be provided, because the surfaces can be connected more easily to fiber bundles.

The light guiding taper can comprise a frustum, wherein a lateral surface of the light guiding taper can comprises a lateral surface of the frustum. A frustum can provide the light guiding taper with a smaller end face and a larger end face. The frustum can be a portion of a right circular cone. The light guiding taper can be the frustum.

A smaller base face of the frustum can be the light entry surface of the light guiding taper and/or a larger base face of the frustrum can be the light emitting surface of the light guiding taper. In this embodiment, the frustum can be a front part and/or a rear part of the light guiding taper or can constitute the entire light guiding taper.

According to an embodiment, the light guiding taper can comprise at least one cylindrical portion abutting the frustum. The at least one cylindrical portion can be arranged in front of or behind the frustum in the direction of light propagation. With the cylindrical portion, the light guiding taper can be elongated in order to better fit into components of the exoscope. For example, the light guiding taper can be elongated in order to better fit into the light source connector of the light guide cable of the exoscope. A length of the cylindrical portion can be at least 50 mm.

A gradient along the lateral surface of the frustum in a direction from the light entry surface to the light emitting surface can be constant. This shape of the frustum can provide the light guiding taper to guide the light in the light guiding taper without significant losses or distortions.

The light guiding taper can be made of or can contain glass or can be made of or can contain a fused glass fiber bundle. Glass can be provided as a material for the light guiding taper as it can be manufactured precisely and can guide the light without significant losses. The inclusion of fibers can also achieve good illumination results.

In an embodiment, the light guide can comprise a first fiber bundle, wherein the light emitting surface of the light guiding taper faces, and can abut, a first end of the first fiber bundle, wherein a second end of the first fiber bundle can be arranged at the light exit end of the illumination optics, wherein the first end of the first fiber bundle can be dimensioned to conform to the surface area of the light emitting surface of the light guiding taper. The medical imaging device body can house at least a part of the first fiber bundle. The first fiber bundle can constitute the final part of the light path, before the light exits from the tip or distal surface of the medical imaging device. The first fiber bundle can be optically cemented to the light emitting surface.

In an embodiment that can be combined with the previous embodiment or used on its own, the light guide can comprise a second fiber bundle, wherein the light entry surface of the light guiding taper faces, and can abut, a second end of the second fiber bundle, wherein a first end of the second fiber bundle can be arranged at the light entry end of the illumination optics, wherein the second end of the second fiber bundle can be dimensioned to conform to the surface area of the light entry surface of the light guiding taper. In this case, a fiber bundle can be applied in front of the light guiding taper in the direction of propagation of illumination light from its source to the operating area.

According to an embodiment, the illumination system can comprise a light guide cable, wherein a first end of the light guide cable can comprise a light source connector configured to be connected to the illumination light source, wherein a second end of the light guide cable can be connected to the medical imaging device body or configured to be connected to the medical imaging device body. The light source connector can be shaped to fit into the light source port of the light source. In one embodiment, the light guide cable can be fixed permanently to the medical imaging device body. In a different embodiment, the light guide cable can be releasably connected to the medical imaging device body, such as with a connector.

According to an embodiment, the second end of the light guide cable can comprise a medical imaging device connector. In this embodiment, the light guide cable can be configured to be releasably connected to the medical imaging device body via the medical imaging device connector. The medical imaging device connector can be configured to be connected to a light guide cable connector on the medical imaging device body.

According to an embodiment, the light guiding taper can be arranged inside the light guide cable, a light guide cable connector, a light source connector of the light guide cable or inside a medical imaging device comprising a distal part of the illumination optics. The light guide cable connector can be configured to be connected with the medical imaging device connector of the light guide cable. By arranging the light guiding taper inside the light guide cable connector of the medical imaging device body, the distance along the light path from the light emitting surface of the light guiding taper to the medical imaging device tip or front face can be kept short. With such configuration, a cross section of a fiber bundle connecting the light emitting surface with the medical imaging device tip or front face can match a cross section of the light emitting surface. As the light emitting surface has a comparatively large cross section, an equally thick fiber bundle can be required to connect it with the medical imaging device tip or front face. Thus, by keeping the distance short, only the medical imaging device body can be required to house a thick fiber bundle. In contrast, the light guide cable may comprise a thinner fiber bundle, because its cross section only has to match the cross section of the smaller light entry surface. This makes it possible to use a standard light guide cable, for example a light guide cable with a diameter of 4.25 mm. Such standard light guide cables are also used with endoscopes, which can enhance compatibility. In addition, thinner light guide cables are lighter and thus easier to carry.

The light guide cable connector can be a cold light connector, i.e., a light guide connector of a lens or fiber telescope. It is the connector where the light guide cable can be attached to the telescope. Usually, in endoscopes the numerical aperture is increased upon entry into the endoscope. In the present case of open surgery, the numerical aperture can be decreased and therefore the fiber cone has the thinner diameter towards the cable and the thicker diameter towards the distal, i.e., light emitting end.

According to an embodiment, the light entry surface of the light guiding taper can face a second fiber bundle, which can extend from the light source connector through the light guide cable to the medical imaging device connector of the light guide cable. The second fiber bundle thus can run inside the light guide cable from the light source connector to the medical imaging device connector, where it can face the light entry surface of the light guiding taper. In comparison, in this embodiment, the first fiber bundle can run inside the medical imaging device body from the light emitting surface to the medical imaging device tip or front surface. The second fiber bundle can be optically cemented to the light entry surface. The first fiber bundle and/or the second fiber bundle can comprise multiple fibers running parallel to each other.

According to a different embodiment, the light guiding taper can be arranged inside the medical imaging device connector of the light guide cable. In this embodiment, the light guide cable can be configured to be releasably connected to the light guide cable connector of the medical imaging device body.

According to another embodiment, the light guiding taper can be arranged inside the light source connector of the light guide cable, wherein the light entry surface of the light guiding taper can be an entry face of the light source connector. In this embodiment, the entry face of the light source connector can be the light entry end of the illumination optics.

The first fiber bundle can extend from the light emitting surface of the light guiding taper through the light guide cable and the medical imaging device body to the medical imaging device tip or front face. In this embodiment only a single optical interface in the light path can be used, which can be the interface between the light emitting surface and the first end of the first fiber bundle. A second fiber bundle can be eliminated, because the light enters the light guiding taper directly from the light source. By omitting the second fiber bundle, losses in light intensity at optical interfaces can be reduced.

Such object can be further solved by a medical imaging system for fluorescence imaging in open surgery comprising an illumination system according to one of the previously described embodiments and a medical imaging device. The same or similar advantages, features and characteristics apply to the medical imaging system as were previously mentioned with respected to the illumination system. The illumination light source can comprise a light source port configured to be connected to a light source connector of a light guide cable.

In embodiments, the medical imaging device can be an exoscope or a fluorescence imaging adapter connected with or capable of being connected with a camera head.

The medical imaging device can be part of the illumination optics. The illumination optics can comprise a light guide cable, the light guide cable being one of connectable to an illumination light entry port of the medical imaging device and integral with the medical imaging device.

BRIEF DESCRIPTION OF THE DRAWINGS

Further characteristics will become apparent from the description of the embodiments together with the claims and the included drawings. Embodiments can fulfill individual characteristics or a combination of several characteristics.

The embodiments are described below, without restricting the general intent of the invention, based on the exemplary embodiments, wherein reference is made expressly to the drawings with regard to the disclosure of all details that are not explained in greater detail in the text. In the drawings.

In the drawings, the same or similar types of elements or respectively corresponding parts are provided with the same reference numbers in order to prevent the item from needing to be reintroduced.

DETAILED DESCRIPTION

Figure 1:
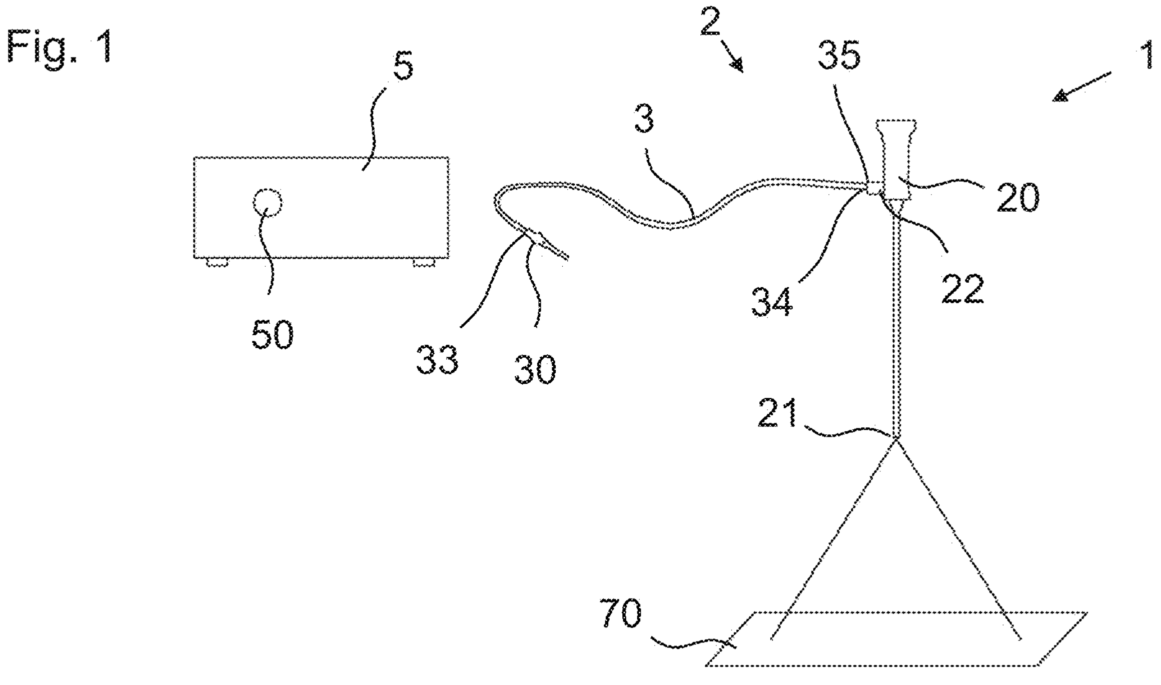
FIG. 1 illustrates a schematic simplified representation of an exoscope system comprising a light source and an exoscope with a light guide cable.

FIG. 1 shows a schematically simplified representation of an exoscope system 1 used for open surgery as a first example of a medical imaging system. The exoscope system 1 comprises an illumination light source 5 and an exoscope 2 with a light guide cable 3. The light guide cable 3 may be part of the exoscope 2 or separate to the exoscope 2. The exoscope 2 is configured to image an operating area 70 with an optical imaging unit (e.g., image sensor) not shown in FIG. 1. In order to illuminate the operating area 70 when observing it, the exoscope 2 further comprises illumination optics configured to guide light from the illumination light source 5 to an exoscope tip 21 of the exoscope 2. To this end, the light source 5 comprises a light source port 50 configured to receive a light source connector 30 arranged at a first end 33 of the light guide cable 3. The second end 34 of the light guide cable 3 is connected to an exoscope body 20 of the exoscope 2. In the exemplary embodiment shown in FIG. 1, this is done with an exoscope connector 35 of the light guide cable 3 and a light guide cable connector 22 of the exoscope body 20. With these connectors 22, 35, the light guide cable 3 is detachable from the exoscope body 20. According to a different embodiment not shown in FIG. 1, the exoscope body 20 and the light guide cable 3 form a single unit and are not detachable from each other.

Inside the light guide cable 3 and the exoscope body 20, illumination light is guided through fiber bundles. However, as the illumination light exits the fiber bundle at the exoscope tip 21, an irradiance distribution of the light is usually too broad for the observed operating area 70. Thus, only a part of the emitted light actually illuminates the operating area 70. This is undesired, because it lowers the light intensity inside the operating area 70.

Figure 2:
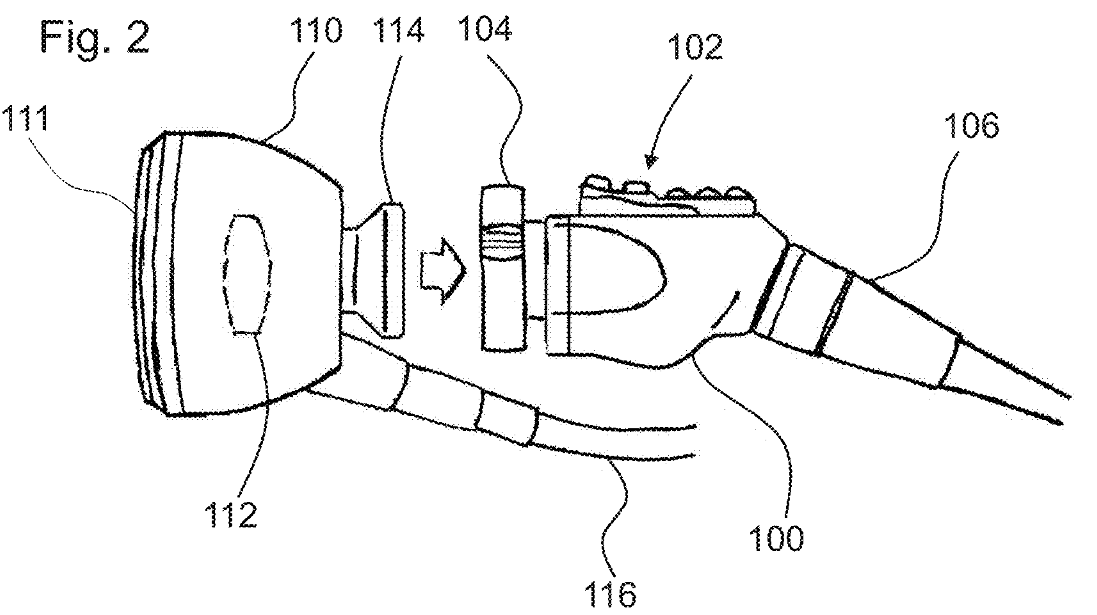
FIG. 2 illustrates a schematic simplified representation of a camera head with a fluorescence imaging adapter.

FIG. 2 illustrates a schematic representation of another medical imaging device, namely a combination of a camera head 100 and a fluorescence imaging adapter 110. The camera head 100 is configured for white light imaging as well as fluorescence imaging. It is handheld and has control buttons 102 on the top of its housing, an adapter 104 for attachment of various optics systems at its front surface and a connecting cable 106 for power and signal transmission leading to a central control unit (not shown). Since the camera head 100 is configured to receive telescope type endoscopes with eyepieces (ocular cones), its adapter 104 may be configured to receive such eyepieces. The imaging optics of the camera head 100 is configured to have its focus at a location where the typically attached endoscopes project a virtual image to be viewed with the naked eye through the eyepiece. The eyepieces of endoscopes are usually adjusted so that the virtual image is about one meter in front of the eyepiece (−1 diopter). The exit pupil of the endoscopes is configured to approximately match the entrance pupil of the camera head and is located about 7 mm behind the edge of the eyepiece funnel, which is typically inside adapter 104 in the attached state.

The fluorescence imaging adapter 110 differs from endoscopes and exoscopes in that it does not have imaging optics, i.e., it does not produce a virtual image. Instead, it provides a head lens or attachment lens in the form of a head lens system 112 having one or more individual lenses whose function it is to change the properties of the imaging optics of camera head 100, rendering the camera head 100 capable of viewing the operating field. This can be done, e.g., by decreasing the focal length of the camera head 100 and thereby enlarging its field of view. Although the head lens system 112 itself does not provide a virtual image to be viewed with the naked eye, the fluorescence imaging adapter has a standardized ocular cone 114 on its rear side for the purpose of connecting to the adapter 104 of camera head 100.

Furthermore, the fluorescence imaging adapter 110 is equipped with a light guide cable 116 leading towards its front surface 111. The other end of the light guide cable 116 may be connected to an illumination light source 5 as shown in FIG. 1.

Figure 3:
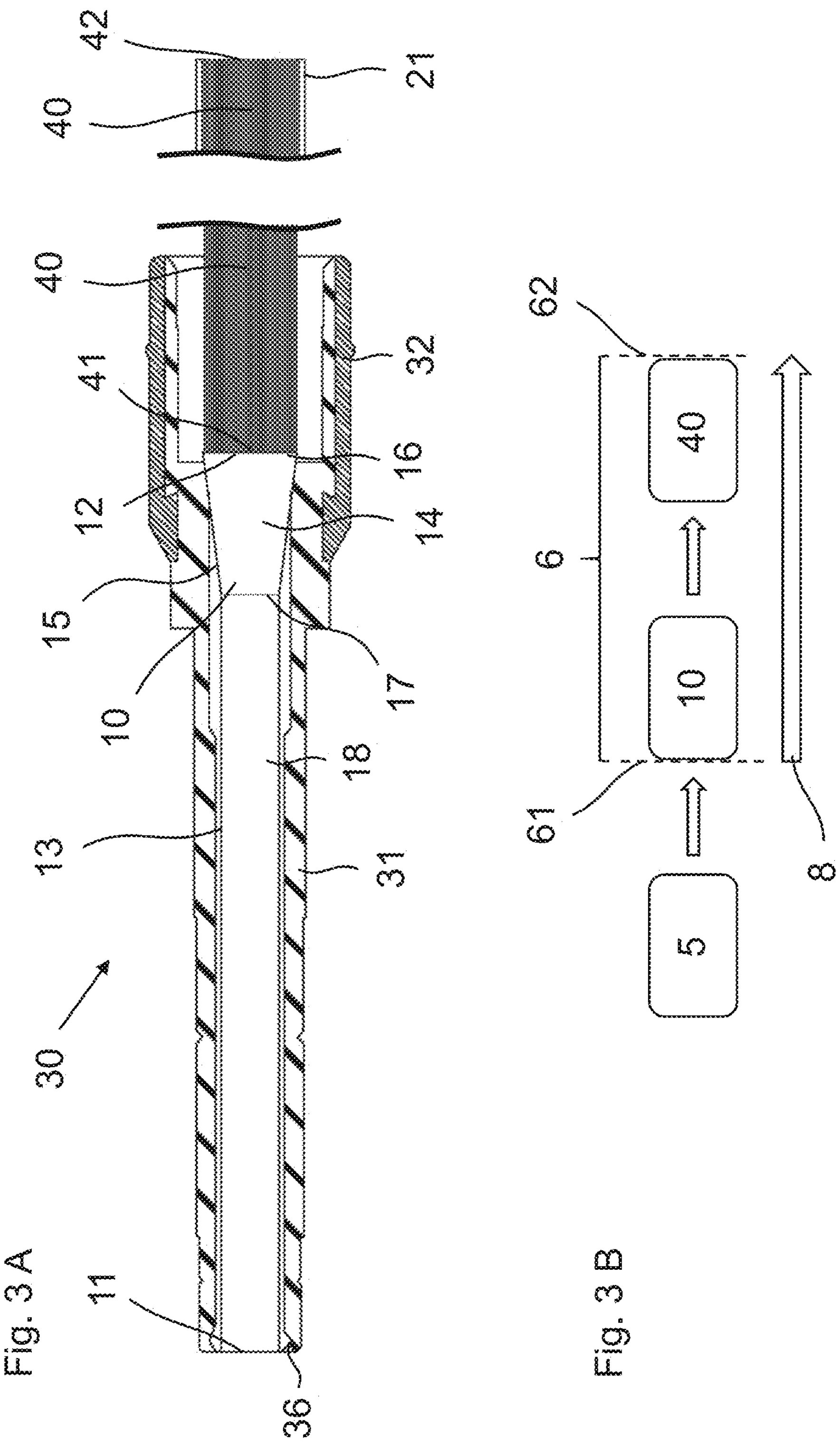
FIG. 3A illustrates a schematic simplified cross sectional representation of a first embodiment of a light guiding taper arranged inside a light source connector.
FIG. 3B illustrates a schematic simplified representation of the illumination optics and the light path in the embodiment of FIG. 3A.

FIG. 3A illustrates a schematic simplified cross sectional view of an embodiment of a light source connector 30 of the light guide cable 3 configured to solve this problem. The light source connector 30 comprises different connector shell parts 31, 32, which enclose a first fiber bundle 40 and a light guiding taper 10. The light guiding taper 10 is formed from glass or similar material or a fused glass fiber bundle. In the embodiment shown in FIG. 3A, the light guiding taper 10 has a cylindrical portion 18 and a frustum 14, whose interface is indicated by a dotted line. A light entry surface 11 of the light guiding taper 10 acts as an entry face 36 of the light source connector 30, so that light entering the light source connector 30 from the light source port 50 is immediately entered into the light guiding taper 10. A light emitting surface 12 of the light guiding taper 10 abuts a first end 41 of the first fiber bundle 40. The first fiber bundle 40 extends from the first end 41 in the light source connector 30 through the entirety of the light guide cable 3 and the exoscope body 20 to a second end 42 in the exoscope tip 21, where the light is emitted.

The lateral surface 13 of the light guiding taper 10 consists of a lateral surface of the cylindrical portion 18 and a lateral surface 15 of the frustum 14. The smaller base face 17 of the frustum 14 abuts the cylindrical portion 18, while the larger base face 16 constitutes the light emitting surface 12. The cylindrical portion 18 allows the light guiding taper 10 to fit into the light source connector 30 in such a way, that the light entry surface 11 forms the entry face 36 of the light source connector 30.

Due to the frustum 14, an area of the light emitting surface 12 is larger than an area of the light entry surface 11. Due to the optical law of Etendue invariance, according to which the mathematical product of the illuminating area and the solid angle of illuminance remains constant in an illumination chain, a light exit solid angle at the light emitting surface 12 will be smaller than a light entry solid angle at the light entry surface 11. Thus, when exiting the exoscope tip 21 or the front face of fluorescence imaging adapter 110 of FIG. 2, the irradiance distribution will be narrowed down and the light intensity in the operating area 70 will be increased.

As the first fiber bundle 40 runs through the entire light guide cable 3 and the medical imaging device body 20, 110 in this embodiment, the light guide cable 3 and the medical imaging device body 20, 110 will usually form a single unit and are not detachable.

FIG. 3B shows a schematic simplified representation of illumination optics 6 of the embodiment shown in FIG. 3A, comprising the light guiding taper 10 and the first fiber bundle 40. Light entering from the light source 5 is guided through the light guiding taper 10 and the first fiber bundle 40 to the exoscope tip 21 or front face of fluorescence imaging adapter 110. Thus, a light path 8 through the illumination optics 6 extends from a light entry end 61 at the light entry surface 11 to a light exit end 62 at the second end 42 of the first fiber bundle 40. As the illumination optics 6 comprise only a single optical interface between the light guiding taper 10 and the first fiber bundle 40, a loss of light intensity is low in this embodiment.

Figure 4:
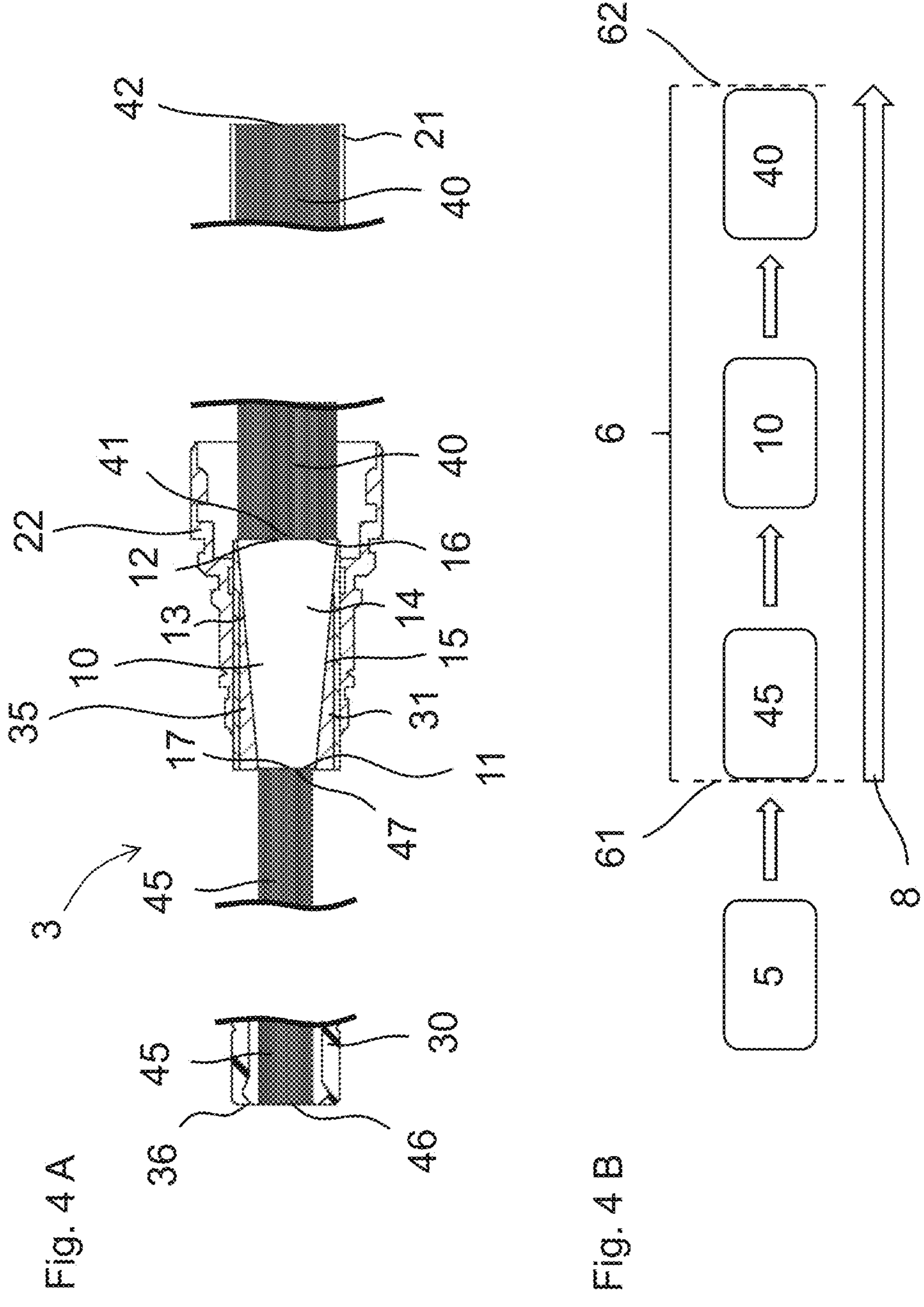
FIG. 4A illustrates a schematic simplified cross sectional representation of a second embodiment of a light guiding taper arranged inside a light guide cable connector of a medical imaging device body.
FIG. 4B illustrates a schematic simplified representation of the illumination optics and the light path in the embodiment of FIG. 4A.

FIG. 4A shows a schematic simplified cross sectional view of another embodiment of the light guiding taper 10. In this embodiment, the light guiding taper 10 is arranged inside the medical imaging device connector 35. In FIG. 4A, the medical imaging device connector 35 of the light guide cable 3 is connected to the light guide cable connector 22. A second fiber bundle 45 is arranged inside the light guide cable 3, which extends from a first end 46 at the entry face 36 of the light source connector 30 to a second end 47. When the light guide cable 3 is connected to the exoscope body 20 or the body of the fluorescence imaging adapter 110, this second end 47 faces the light entry surface 11 of the light guiding taper 10. The light emitting surface 12 of the light guiding taper 10 abuts the first end 41 of the first fiber bundle 40, which in this embodiment extends only inside the exoscope body 20 to the exoscope tip 21 or the fluorescence imaging adapter 110 to its front face. Unlike the embodiment shown in FIG. 3A, the light guiding taper 10 shown in FIG. 4A does not comprise a cylindrical portion 18. The cylindrical portion 18 can be omitted in this embodiment, as it is not required in order for the light guiding taper 10 to fit into the medical imaging device connector 35.

The arrangement shown in FIG. 4A may also be reversed, such that the light guiding taper 10 may be arranged inside the light guide cable connector 22, which then would be the smaller of the two connectors 22, 35, with medical imaging device connector 35 configured to be fitted over light guide cable connector 22.

In the embodiment of FIG. 4A, the light guide cable 3 can be configured to be detachable, because there is no single fiber bundle extending through both the light guide cable 3 and the exoscope body 20 or the fluorescence imaging adapter 110. In addition, a standard light guide cable 3 with a diameter smaller than the diameter of the light guide cable 3 in FIG. 2*a* can be utilized, because the diameter of the second fiber bundle 45 does only need to match the light entry surface 11, not the larger light emission surface 12.

FIG. 4B shows a schematic simplified representation of the illumination optics 6 of the embodiment of FIG. 4A. According to a first definition, the illumination optics 6 comprise the second fiber bundle 45, the light guiding taper 10 and the first fiber bundle 40. Thus, unlike the illumination optics 6 according to FIG. 3B, the light path 8 in FIG. 4B crosses one additional optical interface. According to a different definition, the light path 8 and the illumination optics 6 in FIG. 4B only comprise the light guiding taper 10 and the first fiber bundle 40. Thus, in this definition the light entry end 61 is not at the first end 46 of the second fiber bundle 45, but at the light entry surface 11 of the light guiding taper 10.

Figures 5, 6:
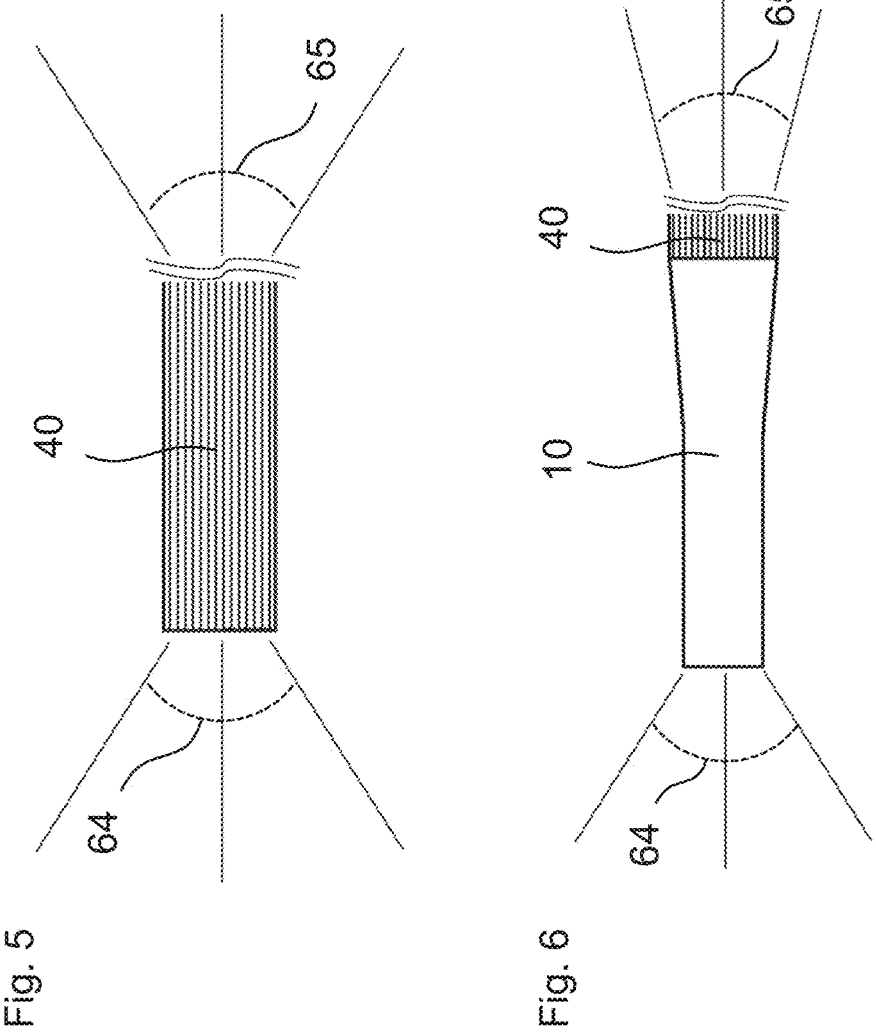
FIG. 5 illustrates a schematic simplified representation of a light entry solid angle and a light exit solid angle for a fiber bundle.
FIG. 6 illustrates a schematic simplified representation of a light entry solid angle and a light exit solid angle with a light guiding taper.

FIG. 5 shows a schematic simplified representation of a light entry solid angle 64 and a light exit solid angle 65 for the first fiber bundle 40. As the first fiber bundle 40 does not change its diameter, the light entry solid angle 64 will be the same as the light exit solid angle 65. For example, both angles may be 40°.

FIG. 6 shows a schematic simplified representation of the light entry solid angle 64 and the light exit solid angle 65 for the light guiding taper 10. The light entry solid angle 64 is the same as in FIG. 4, for example 40°. However, because the light emitting surface 12 of the light guiding taper 10 is larger than its light entry surface 11, the light exit solid angle 65 of the light guiding taper 10 and of the abutting first fiber bundle 40 is decreased, for example to an angle of 32.5°.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCES

1 exoscope system
2 exoscope
3 light guide cable
5 illumination light source
6 illumination optics
8 light path
10 light guiding taper
11 light entry surface
12 light emitting surface
13 lateral surface
14 frustum
15 lateral surface
16 larger base face
17 smaller base face
18 cylindrical portion
20 exoscope body
21 exoscope tip
22 light guide cable connector
30 light source connector
31, 32 connector shell part
33 first end
34 second end
35 medical imaging device connector
36 entry face
40 first fiber bundle
41 first end
42 second end
45 second fiber bundle
46 first end
47 second end
50 light source port
61 light entry end
62 light exit end
64 light entry solid angle
65 light exit solid angle
70 operating area
100 camera head
102 control buttons
104 adapter for attachment devices
106 connecting cable
110 fluorescence imaging adapter
111 front surface
112 head lens system
114 ocular cone
116 light guide cable

What is claimed is:

1. An illumination system for fluorescence imaging in open surgery, the illumination system comprising:

an illumination light source configured to generate illumination light including white light and fluorescence excitation light, and illumination optics for illuminating an operating area with the illumination light generated by the illumination light source, the illumination optics comprising a light guide configured for guiding illumination light from the illumination light source coupled into a light entry end of the illumination optics along a light path of the illumination optics to a light exit end of the illumination optics, wherein the light guide comprises a light guiding taper arranged in the light path, the light guiding taper being configured to narrow an irradiance distribution by decreasing the solid angle of light exiting the light exit end of the illumination optics, the light guiding taper comprising a light entry surface oriented towards or located at the light entry end of the illumination optics and a light emitting surface oriented towards or located at the light exit end of the illumination optics, wherein an area of the light emitting surface is larger than an area of the light entry surface.

2. The illumination system according to claim 1, wherein one or more of the light entry surface and the light emitting surface are circular.

3. The illumination system according to claim 1, wherein the light entry surface and the light emitting surface are parallel to each other.

4. The illumination system according to claim 1, wherein the light guiding taper comprises a frustum, wherein a lateral surface of the light guiding taper comprises a lateral surface of the frustrum.

5. The illumination system according to claim 4, wherein one or more of a smaller base face of the frustum is the light entry surface of the light guiding taper and a larger base face of the frustrum is the light emitting surface of the light guiding taper.

6. The illumination system according to claim 4, wherein the light guiding taper comprises at least one cylindrical portion abutting the frustum.

7. The illumination system according to claim 4, wherein a gradient along the lateral surface of the frustum in a direction from the light entry surface to the light emitting surface is constant.

8. The illumination system according to claim 1, wherein the light guiding taper is made of or contains glass or is made of or contains a fused glass fiber bundle.

9. The illumination system according to claim 1, wherein the light guide comprise a first fiber bundle, the light emitting surface of the light guiding taper is oriented towards and aligned with a first end of the first fiber bundle, a second end of the first fiber bundle is arranged at the light exit end of the illumination optics.

10. The illumination system according to claim 9, wherein the light emitting surface of the light guiding taper abuts the first end of the first fiber bundle.

11. The illumination system according to claim 9, wherein the first end of the first fiber bundle is dimensioned to conform to the surface area of the light emitting surface of the light guiding taper.

12. The illumination system according to claim 9, wherein the light guide comprises a second fiber bundle, wherein the light entry surface of the light guiding taper is oriented towards and aligned with a second end of the second fiber bundle, a first end of the second fiber bundle is arranged at the light entry end of the illumination optics.

13. The illumination system according to claim 12, wherein one of:

the light entry surface of the light guiding taper abuts the second end of the second fiber bundle; or the second end of the second fiber bundle is dimensioned to conform to the surface area of the light entry surface of the light guiding taper.

14. The illumination system according to claim 1, further comprising a light guide cable, wherein a first end of the light guide cable comprises a light source connector configured to be connected to the illumination light source, a second end of the light guide cable is connected to the medical imaging device body or configured to be connected to the medical device imaging body.

15. The illumination system according to claim 11, wherein the second end of the light guide cable comprises a medical imaging device connector.

16. The illumination system according to claim 1, wherein the light guiding taper is arranged inside one of a light guide cable, a light guide cable connector, a light source connector of the light guide cable or inside a medical imaging device comprising a distal part of the illumination optics.

17. A medical imaging system for fluorescence imaging in open surgery comprising:

an illumination system according to claim 1; and a medical imaging device.

18. The medical imaging system according to claim 17, wherein the medical imaging device is one of an exoscope or a fluorescence imaging adapter configured to be connected with a camera head.

19. The medical imaging system according to claim 18, wherein the medical imaging device is part of the illumination optics.

20. The medical imaging system according to claim 19, wherein the illumination optics comprises a light guide cable, the light guide cable being configured to be connected to an illumination light entry port of the medical imaging device and integral with the medical imaging device.

21. An illumination system for fluorescence imaging in open surgery, the illumination system comprising:

an illumination light source configured to generate illumination light including white light and fluorescence excitation light, and illumination optics for illuminating an operating area with the illumination light generated by the illumination light source, the illumination optics comprising a light guide configured for guiding illumination light from the illumination light source coupled into a light entry end of the illumination optics along a light path of the illumination optics to a light exit end of the illumination optics, wherein the light guide comprises a light guiding taper arranged in the light path, the light guiding taper comprising a light entry surface oriented towards or located at the light entry end of the illumination optics and a light emitting surface oriented towards or located at the light exit end of the illumination optics, wherein an area of the light emitting surface is larger than an area of the light entry surface, the light guide comprises a first fiber bundle, the light emitting surface of the light guiding taper is oriented towards and aligned with a first end of the first fiber bundle, a second end of the first fiber bundle is arranged at the light exit end of the illumination optics, and the light guide comprises a second fiber bundle, wherein the light entry surface of the light guiding taper is oriented towards and aligned with a second end of the second fiber bundle, a first end of the second fiber bundle is arranged at the light entry end of the illumination optics.

* * * * *